United States Patent [19]

Mori et al.

[11] Patent Number: 4,737,707
[45] Date of Patent: Apr. 12, 1988

[54] HUMIDITY SENSOR

[75] Inventors: Keijiro Mori, Kanagawa; Hideaki Yagi, Kasugai; Ichiro Shimano, Kanagawa; Tooru Onouchi, Naka, all of Japan

[73] Assignees: Matsushita Electric Industrial Co., Ltd., Osaka; NGK Spark Plug Company, Aichi; Matsushita Seiko Co., Ltd., Osaka, all of Japan

[21] Appl. No.: 834,308
[22] PCT Filed: Jun. 18, 1985
[86] PCT No.: PCT/JP85/00342
§ 371 Date: Apr. 21, 1986
§ 102(e) Date: Apr. 21, 1986
[87] PCT Pub. No.: WO86/00409
PCT Pub. Date: Jan. 16, 1986

[30] Foreign Application Priority Data

Jun. 21, 1984 [JP] Japan .................. 59-128058
Jun. 21, 1984 [JP] Japan .................. 59-128059

[51] Int. Cl.⁴ ............................................ G01W 1/11
[52] U.S. Cl. .................... 324/61 R; 73/335; 340/602; 324/61 R
[58] Field of Search ............ 324/61 P, 61 R, 464, 324/468; 340/602, 627, 632; 73/335

[56] References Cited

U.S. PATENT DOCUMENTS 2,834,201 5/1958 Ohlheiser ............................ 73/335
2,954,445 9/1960 Hargreaves ..................... 340/602 X
4,063,897 12/1977 Aoki.

FOREIGN PATENT DOCUMENTS 56-113328 1/1983 Japan.
0022944 2/1983 Japan ..................... 73/335
57-47890 9/1983 Japan.
0204742 11/1984 Japan ..................... 340/602

Primary Examiner—Reinhard J. Eisenzopf
Assistant Examiner—Robert W. Mueller
Attorney, Agent, or Firm—Wenderoth, Lind & Ponack

[57] ABSTRACT

A humidity sensing portion (7) and an electrode (9) of a heating regeneration type humidity sensor provided with a heater (8) are covered by a casing (12) and a holding portion (11). An opening (6) for communication between placing the interior and exterior of the sensor in communication is formed in the casing (12) or the holding portion (11) so that a solid angle, of a vertex at the central portion of the humidity sensing portion (7) or the casing (12) of a polyhedron having a base bounded by the opening is within the range of 1/1000–1/10 radian, and thus, adhesion of harmful substances, especially inorganic harmful substances, onto the humidity sensing portion (7) or the electrode (9) is prevented.

6 Claims, 5 Drawing Sheets

Solid angle of opening S x $10^{-3}$ (Radian)

Fig. 3(a)
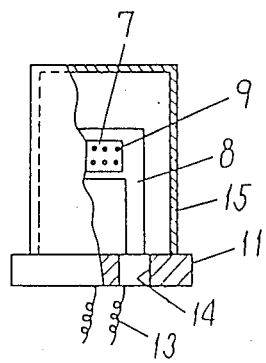
Fig. 3(b)
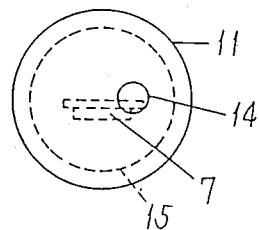
Fig. 4(a)     Fig. 4(b)     Fig. 4(c)
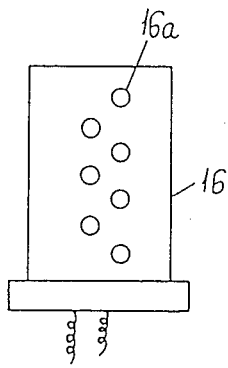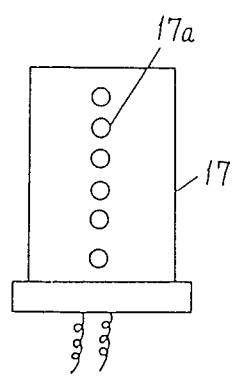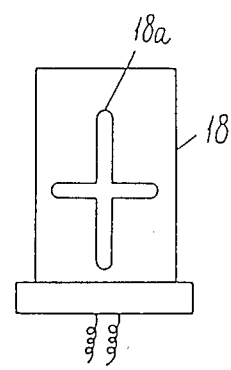

HUMIDITY SENSOR

BACKGROUND OF THE INVENTION

1. Field of the Invention

The present invention relates to a humidity sensor employed for measuring humidity in the atmosphere or humidity control.

2. Description of the Related Art

Conventionally, for the measurement of humidity, there have beem employed a hair hygrometer, wet and dry bulb hydrometers or the like. However, due to the recent progress in the field of electronic techniques, electrical measurements are brought into application due to simplicity in operation. In the electrical measurements referred to above, materials whose resistance values or dielectric constants vary depending on humidity are employed to convert the humidity variations into quantities of electricity due to variations in the resistance values or dielectric constants. By way of example, as the materials whose resistance values are altered, metallic oxides or ceramics are employed, while for the materials whose dielectric constants are varied, organic films may be used. However, since these humidity sensors are arranged to detect the humidity through contact thereof with the atmosphere, there has been a disadvantage in that the characteristics of the humidity sensors are deteriorated by adhesion of atmospheric pollutants to the surfaces of the humidity sensors.

Therefore, it has been a recent practice to prevent the deterioration of the humidity sensor characteristics by a heating regeneration method in which harmful substances adhering to the surface of the humidity sensor are removed by heating the sensor at high temperatures or by a method in which the humidity sensor is covered by a surface soiling prevention filter. Such a surface soiling prevention filter is mainly applied to an organic film type sensor which can not be subjected to the heating regeneration, while the heating regeneration method is utilized for the humidity sensor employing ceramics.

The humidity sensor to which such heating regeneration is applied will be described hereinbelow with reference to FIG. 10.

In FIG. 10, an electrode 3 is fixed on a surface of a humidity sensing portion 1 composed of ceramics and the like, while a heater 2 is attached to its surface confronting this electrode 3. The humidity sensing portion 1, heater 2 and electrode 3 are fixed to a holding portion 4, and a protector 5 enclosing these parts for protection thereof against mechanical damages is secured to the holding portion 4. This protector 5 is formed with a large number of through-holes 5a in its peripheral face for improved heat radiation. Moreover, lead wires 6 electrically connected with the electrode 3 are connected with the electrode 3 through the holding portion 4.

When the humidity sensor having the construction as described above is brought into contact with the measuring atmosphere, water vapor in the atmosphere arrives at the humidity sensing portion 1 by diffusion or by air stream so as to be absorbed thereonto, and depending on the amount of absorption at that time, the humidity sensing portion 1 undergoes a variation in its electrical characteristics. If the variation is preliminarily applied in the form of voltage to the electrode 3 through the lead wires 6, humidity in the atmosphere may be electrically detected. Meanwhile, when the characteristics of the humidity sensor are deteriorated by the adhesion of harmful substances onto the surface of the humidity sensing portion 1, it has been a practice to restore the characteristics by heating the humidity sensing portion 1 through energization of the heater 2 so as to burn the adhering harmful substances into the form of a gas for removal.

However, in the conventional humidity sensor, harmful substances are also drawn in together with the atmosphere via the through-holes 5a of the protector 5 to adhere to the humidity sensing portion 1. Such harmful substances may be broadly divided into the harmful substances of organic nature such as soot, smoke of cigarettes, etc. and also into those of inorganic nature such as salt particles, dust, etc. Although removal of organic harmful substances can be effectively made by the heater 2, such heating is hardly effective for the inorganic harmful substances such as salt particles, dust and the like which can not be formed into a gas by combustion for removal. Moreover, since the heater 2 is subjected to high temperatures above 500° C., the protector covering the heater 2 is also heated up to a high temperature, and if any combustible material is located close to the protector 5, there is such a danger that the combustible material is ignited. Furthermore, there is also such a problem in that, if the humidity sensor is provided in a combustible gas atmosphere, an explosion may take place by the heat of the heater 2.

SUMMARY OF INVENTION

Therefore, according to the present invention, the humidity sensing material is enclosed by a holding portion and a casing, with an opening being provided in said holding portion or casing for placing the interior and exterior of the holding portion in communication, and said opening has a solid angle in the range of 1/1000 to 1/10 of a radian, i.e. an opening defining a boundary of the base of a polyhedron and subtending a solid angle between 1/1000 and 1/10 of a radian at a vertex of the polyhedron, the vertex being located at the central portion of the humidity sensing portion or the casing, to prevent entry of the harmful substance detrimental to said humidity sensing portion for preventing the deterioration thereof.

BRIEF DESCRIPTION OF THE DRAWINGS

FIG. 3(a) is a longitudinal cross-section artly broken away, showing a humidity sensor according to a second embodiment of the present invention, FIG. 3(b) is a bottom plan view of the sensor of FIG. 3(a), FIGS. 4(a), 4(b) and 4(c) respectively show side elevational views of humidity sensors according to third, fourth and fifth embodiments of the present invention.

DETAILED DESCRIPTION OF THE PREFERRED EMBODIMENTS

Hereinafter, preferred embodiments of the present invention will be described with reference to FIGS. 1 through 8.

Figure 1A:
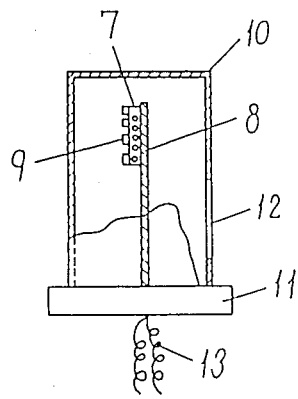
FIG. 1(a) is a longitudinal cross-sectional view partly broken away, showing a humidity sensor according to one preferred embodiment of the present invention.
Figure 1B:
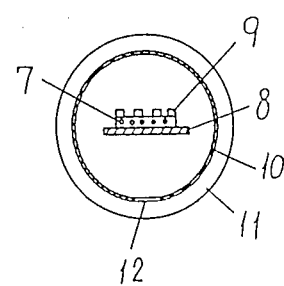
FIG. 1(b) is a lateral cross-section of the sensor of FIG. 1(a)

FIGS. 1(a) and 1(b) show a humidity sensor according to a first embodiment of the present invention. In FIGS. 1(a) and 1(b), numeral 7 denotes a humidity sensing portion for detecting the humidity, numeral 8 denotes a heater for cleaning by heating the humidity sensing portion 7, and numeral 9 denotes an electrode for converting the humidity into electrical signals. The humidity sensing portion 7, heater 8 and electrode 9 are accommodated in a cylindrical casing 10 a bottom, with the casing 10 being closed by a disc-like holding portion 11 to which the heater 8 is mounted. This casing 10 is formed with a slit-like opening 12. To the holding portion 11, the humidity sensing portion 7 and the heater 8 are fixed. The opening 12 is intended to allow the humidity sensing portion 7 to contact the atmosphere. This opening 12 is located below the humidity sensing portion 7 and the electrode 9 subtends a solid angle of a vertex of a polyhedron, the vertex at the central portion of the humidity sensing portion 7 and/or casing 10 and the base of the polyhedron defined by the opening 12, of less than 1/10 of a radian. Numeral 13 denotes lead wires for voltage impression and signal output, which extend from the electrode 9 through the holding portion 11.

With respect to the humidity sensor having the construction as described above, the operation thereof will be described hereinbelow.

Figure 2:
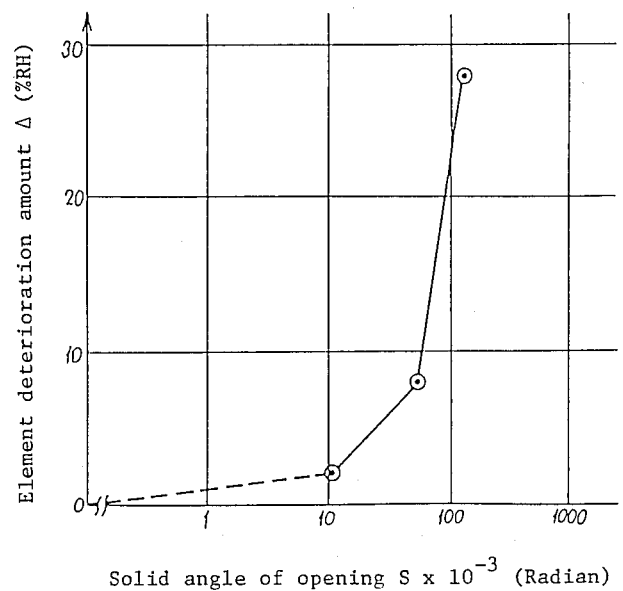
FIG. 2 is a graph showing the relation between solid angles of the opening and deterioration of the element when sea water is sprayed onto the humidity sensor.

In the construction as described so far, if the opening 12 is provided at a predetermined position, so as to extend vertically downwardly, the humidity sensing portion 7 and the electrode 9 are covered by the casing 10 in the surrounding portion thereof, and are brought into contact with the atmosphere only through the slit-like opening 12 located thereunder for the detection of the humidity. With the above arrangement, since the inorganic solid particles such as salt particles, dust, etc. in the atmosphere can not move through the atmosphere by diffusion as in water vapor such particles do not adhere to the humidity sensing portion 7 and the electrode 9 even if they enter through the opening 12 in a windless state, and freely drop so as to merely accumulate onto the upper portion of the casing 10 at the most. Moreover, even in the presence of wind, since the solid angle of the opening 12 is less than 1/10 of a radian, with said opening being provided only at one side with respect to the direction of the wind, ventilation is not readily established. Meanwhile, even if wind should be directed from a vertically upward direction, the harmful particles do not readily adhere to the humidity sensing portion 7 and the electrode 9, since the opening 12 is located in a position lower than said humidity sensing portion 7 and electrode 9. As described above, the humidity sensing portion 7 and the electrode 9 can be protected against adhesion of the inorganic solid particles in any of the above states. FIG. 2 is a graph showing the relation between the solid angles of the opening 12 and the deterioration of the sensor when sea water is sprayed with respect to the opening 12 of the humidity sensor in a directly lateral direction at a wind velocity of about 0.55 m/s. As shown in FIG. 2, it is understood that, by setting the solid angle thereof smaller than 1/10, deterioration of the sensor by the salt component in the presence of wind can be markedly reduced.

On the other hand, water vapor in the atmosphere is absorbed onto the humidity sensing portion 7 through the opening 12 by diffusion even in the windless state, and in that case, varies the electrical characteristics of the portion 7 according to the amount of absorption. The variation in the resistance of portion 7 is converted into electrical signals by the electrode 9 supplied with voltage through the lead wires 13. In the manner described above, the sensor is protected against adhesion of inorganic solid particles in the atmosphere, and detects the humidity in the atmosphere.

In FIGS. 3(a) and 3(b), there is shown a second embodiment according to the present invention. Since the humidity sensing portion 7, heater 8, electrode 9, holding portion 11, and lead wires 13 are the same as those in the first embodiment, like parts are designated by like reference numerals, with detailed description thereof being omitted for brevity. The difference thereof from the first embodiment resides in an opening 14. More specifically, the opening 14 is provided not in the casing 15, but in the holding portion 11. By this construction, the humidity sensing portion 7 and the electrode 9 are completely covered by the casing 15 without any opening so as not to be affected to a substantial degree by the state of a surrounding air stream so as to be protected against the adhesion of inorganic solid particles. Moreover, if the above opening 14 is commonly used with the through-opening for the lead wires 13, it is advantageous from the viewpoint of the manufacture of the humidity sensor.

Figure 5:
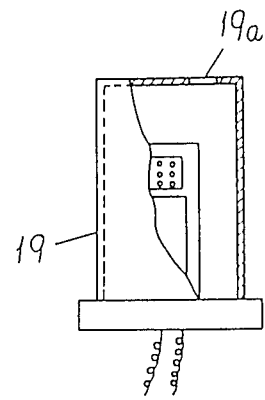
FIG. 5 is a longitudinal cross-sectional view partly broken away, showing a humidity sensor according to a sixth embodiment of the present invention, 4FIG. 6(a) is a longitudinal cross section partly broken away, showing a humidity sensor according to a seventh embodiment of the present invention.

It is to be noted here that, if the solid angle of each opening is limited within the range of 1/10-1/1000, the position, configuration, number, and state of the of openings may be modified as shown in FIGS. 4 and 5. More specifically, in FIG. 4(a), there is shown a third embodiment in which a plurality of openings 16a are formed on the side face of the casing 16 in two rows in a longitudinal direction. FIG. 4(b) shows a fourth embodiment in which openings 17a are formed on the casing 17 in one row in a longitudinal direction. FIG. 4(c) shows a fifth embodiment in which openings 18a are formed on the side face of the casing 18 in the form of a cross. Furthermore, FIG. 5 shows a sixth embodiment in which an opening 19a is formed on the upper surface of the casing 19.

Additionally, if the width of the opening in the embodiment as described so far is set to be smaller than 1 mm, the casing may serve as an explosion-proof structure. In other words, even when a flammable substance is present around the sensor during the cleaning by heating or the casing, catches on fire, the fire does not spread towards the outside of the casing due to the small opening width, and thus, a danger of explosion may be prevented.

Figure 6A:
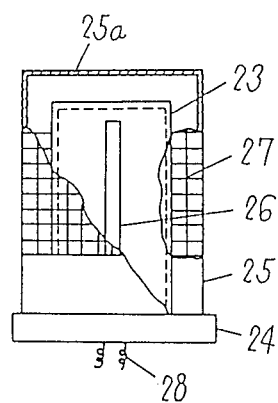
FIG. 6(b) is a lateral cross-sectional view of the sensor of FIG. 6(a)
Figure 6B:
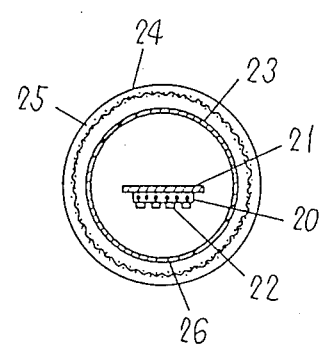

Referring now to FIG. 6, a seventh embodiment according to the present invention will be described hereinbelow. In FIG. 6, numeral 20 denotes a humidity sensing portion for detecting the humidity, numeral 21 denotes a heater for cleaning the humidity sensing portion, and numeral 22 denotes an electrode for converting the humidity into electrical signals. The humidity sensing portion 20, heater 21 and electrode 22 are accommodated in a first casing 23 having a cylindrical configuration with a bottom, and said first casing 23 is closed by a columnar holding portion 24 to which the heater 21 is attached. This first casing 23 has, on its side face, a slit-like opening 26 extending in a longitudinal direction so as to allow the humidity sensing portion 20 to directly contact the atmosphere. The first casing 23 is enclosed in a second casing 25 which is closed at the bottom portion by the holding portion 24, and at the upper portion by a cap 25a, with the side wall being comprised a wire netting. Thus, this second casing 25 is provided with a large number of through-holes 27 each having a width of loss than 1 mm. To the holding portion 24, the humidity sensing portion 20 and the heater 21 are fixed. Lead wires 28 for voltage impression and signal output extend form the electrode 22, and extend through the holding portion 24.

Figure 7:
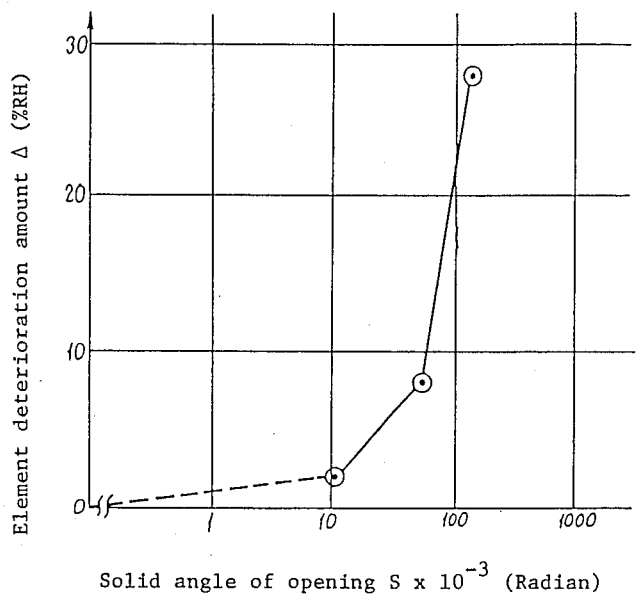
FIG. 7 is a graph showing the relation between solid angles of the opening and deterioration of the element when sea water is sprayed onto the humidity sensor of FIG. 6.

In the above-described embodiment, when the sensor is positioned at the predetermined position, with the opening 26 directed vertically downwardly, the humidity sensing portion 20 and the electrode 22 whose peripheral portions are covered by the first and second casings, contact the atmosphere through the through-holes 27 and the opening 26 to detect the humidity. With the above arrangement, the inorganic solid particles such as salt particles, dust, etc. in the atmosphere, which can not move by diffusion as in water vapor, freely fall in a windless state so as to accumulate on the upper surface of the first and second casings, and do not adhere to the humidity sensing portion 20 and the electrode 22 by entering through the opening 26. Meanwhile, in the presence of wind also, since the opening 26 has a solid angle of less than 1/10 of a radian, and is formed only at one side with respect to the direction of wind so as to prevent an air stream from passing through the sensor, and since said opening 26 is provided below the humidity sensing portion 20 and the electrode 22, harmful particles do not readily adhere to the sensing portion 20 and the electrode 22, even if the wind should blow vertically upwardly. As described above, the humidity sensing portion 20 and the electrode 22 remain substantially free from the adhesion of inorganic solid particles in any of the aforementioned states. FIG. 7 is a diagram showing the relationship between the solid angles of the opening 26 for the first casing and the amount of deterioration of the sensor in the case where sea water is sprayed with respect to the opening 7 from a directly lateral direction at a wind velocity of about 0.55 m/s. As is seen from the diagram, by setting the solid angle at less than 1/10 of a radian, the deterioration of the sensor by the salt particles is markedly reduced even when a wind blows in a lateral direction. Incidentally, when the sensor is deteriorated by the adhesion of organic substances such as tobacco smoke, oil vapor, etc. onto the humidity sensing portion 20 and the electrode 22, it is possible to restore the deteriorated characteristics by removing said organic substances through heating by means of the heater 21.

In this case, however, there may a situation in which the surface of the first casing 23 is excessively heated to about 100° C., with the heater being left energized for a long period of time by some causes. In such a case, since the first casing 23 is covered by the second casing 25, the surface temperature of the second casing 25 can be suppressed to be low as compressed with that of the first casing 23, and there is no danger of fire even if a flammable material such as paper or the like is brought into contact with the second casing 25.

Figure 8:
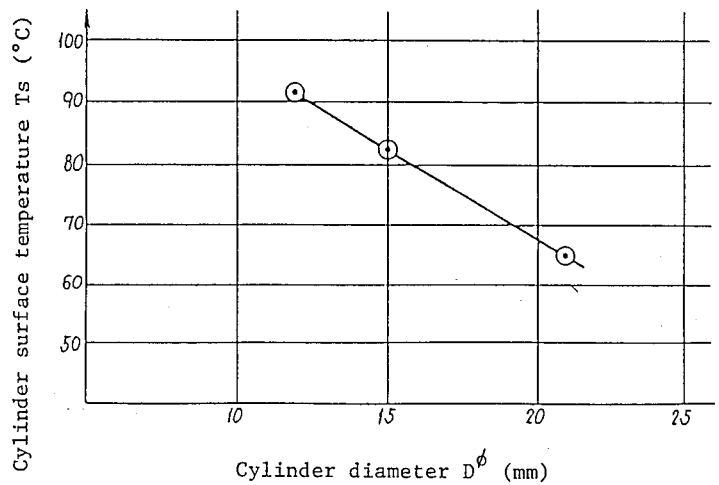
FIG. 8 is a graph showing the relation between a diameter D$\phi$ of a cylinder with a slit for the humidity sensor in FIG. 6 and surface saturated temperature during continuous heating thereof.

FIG. 8 is a graph showing the relation between cylinder surface saturated temperatures and diameters D$\phi$ of cylinders in which a slit-like opening having a width of 1 mm and a length of 30 mm is formed on the side face of a tightly closed cylinder diameter D$\phi$ mm and height of 30 mm, with a heater of 4.5 W being provided in said cylinder for continuous heating under the atmosphere at room temperature of 25° C., and a wind velocity of less than 0.05 m/s. If the diameter D$\phi$ is larger than 20 mm, it becomes possible to reduce the surface temperature lower than 70° C. Accordingly, in the case of cleaning by heating, even when the surface temperature of the first casing is raised above 100° C. by some causes, the surface temperature of the sensor may be limited to be less than 70° C., since the second casing 25 having diameter of about 20 mm and having the large number of through-holes on the side face covers said first casing 23.

As is seen from the foregoing description, according to the humidity sensor of this embodiment, it is possible to detect the humidity in the atmosphere without subjecting the sensor to the problems associated with adhesion of organic solid particles in the atmosphere, and with the sensor outer covering temperature being limited to be below 70° C. at all times during cleaning by heating for safety.

Figure 9A:
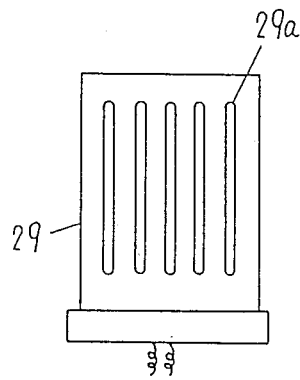
FIGS. 9(a) and 9(b) are side elevational views showing other embodiments of the humidity sensors provided with the second casing of the present invention, FIG. 10 (a) is a longitudinal cross-sectional view partly broken away, showing a conventional humnidity sensor of a heating cleaning type.
Figure 9B:
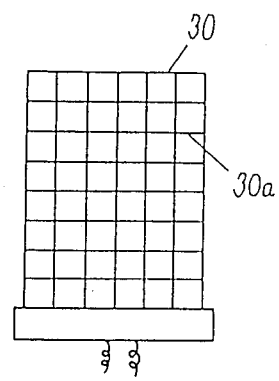
Figure 10A:
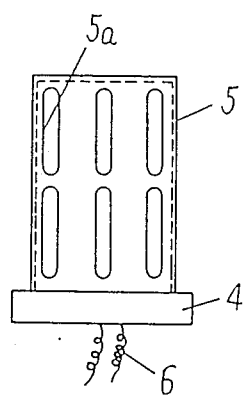
FIG. 10(b) is a lateral cross-sectional view of the sensor of FIG. 10(a).
Figure 10B:
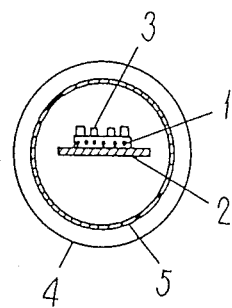

It is to be noted here that in the above seventh embodiment, although the through-holes 27 are provided on the side face of the second casing 25, it may be so modified that a large number of slits 29a are provided on the side face of the second casing 29 as shown in FIG. 9(a). Moreover, as shown in FIG. 9(b), the second casing 30 itself may comprise a net-like form to provide the through-holes 30(b). By using the net-like structure as described above, even when a flammable substance catches fire from the heater in the first casing, spreading of flames outwardly from the second casing 30 is more effectively prevented, thereby to positively improve the explosion-proof property of the sensor.

Furthermore, by forming the sizes of the opening and through-holes in the foregoing embodiment to be less than 1 mm, the explosion proof property is imparted to the first and second casings, and since the sensor as a whole is thus provided with a double explosion proof construction, danger of explosion may be avoided even if any flammable substance is present in the surroundings during cleaning by heating.

As described so far, according to the present invention, due to the arrangement that the opening for placing the interior and exterior of the sensor in communication is formed in the casing enclosing, the humidity sensing portion and the heating portion, or in the holding portion which supports the humidity sensing portion and the heating portion to close the casing, with said opening having a solid angle from the central portion of the humidity sensing portion or the casing in the range of 1/1000–1/10, entry of harmful substances, especially inorganic substances incapable of being regenerated by heat, through the opening can be suppressed, and thus, deterioration of the humidity sensor may be reduced as far as is practicable to prolong the life of the sensor. Accordingly, a humidity sensor, which normally functions for a long period even when used in circumstances full of harmful substances, may be provided, and thus, the range of application of the humidity sensor can be markedly widened.

What is claimed is:

1. A humidity sensor comprising:
   a humidity sensing portion having an electrode;
   a heating portion for heating said humidity sensing portion;
   a holding portion to which the humidity sensing portion and the heating portion are mounted; and
   a casing for enclosing the humidity sensing portion and the heating portion mounted to the holding portion,
   at least one of said casing and said holding portion having an opening extending therethrough for placing space interior of the casing in communication with the ambient temperature exterior of the casing,
   said opening defining the base of a polyhedron having a vortex at the center of the casing, the solid angle of the polyhedron at said vertex being between 1/100 and 1/10 of a radian for inhibiting inorganic substances from entering the interior space of the casing from the atmosphere.

2. A humidity sensor as claimed in claim 1,
   wherein said casing has a double-walled construction comprising a first inner casing through which said opening extends and a second casing extending around said first casing and through which a plurality of through-holes extend.

3. A humidity sensor as claimed in claim 1 or claim 2,
   wherein the opening has a width that is less than 1 mm.

4. A humidity sensor as claimed in claim 1 or claim 2,
   wherein said opening is a slit.

5. A humidity sensor as claimed in claim 1 or claim 2,
   and further comprising at least one other opening extending through the casing, said other opening extending through the casing at a location thereon relative to the location on the casing through which said opening extends which inhibits an air stream originating in the atmosphere from passing through said casing.

6. A humidity sensor as claimed in claim 2,
   wherein said second casing comprises a net-like structure.

* * * * *

UNITED STATES PATENT AND TRADEMARK OFFICE
CERTIFICATE OF CORRECTION

PATENT NO. : 4,737,707
DATED : April 12, 1988
INVENTOR(S) : Keijiro Mori et al.

It is certified that error appears in the above-identified patent and that said Letters Patent is hereby corrected as shown below:

ON THE TITLE PAGE:
In the Assignee Data indicated on the face of the above-identified Patent, "Matsushita Electric Industrial Co., Ltd., NGK Spark Plug Company and Matsushita Seiko Co., Ltd. of Osaka-fu Japan; Aichi-ken, Japan and Osaka-fu Japan, respectively" has been changed to --NGK Spark Plug Company of Aichi-ken, Japan--.

Signed and Sealed this

Fourteenth Day of March, 1989

Attest:

DONALD J. QUIGG

*Attesting Officer*   Commissioner of Patents and Trademarks